United States Patent [19]

Korner et al.

[11] 4,088,124

[45] May 9, 1978

[54] METHOD FOR TREATING PREMATURE INFANTS

[75] Inventors: Anneliese F. Korner; Robert L. Piziali; Orval T. Ellsworth, all of Palo Alto, Calif.

[73] Assignee: The Board of Trustees of Leland Stanford Junior University, Stanford, Calif.

[21] Appl. No.: 760,125

[22] Filed: Jan. 17, 1977

Related U.S. Application Data

[62] Division of Ser. No. 639,288, Dec. 10, 1975, Pat. No. 4,048,684.

[51] Int. Cl.[2] .................... A61B 19/00; A61H 1/00

[52] U.S. Cl. .................... 128/1 B; 128/33; 5/371

[58] Field of Search .................... 128/24.1, 24.2, 33, 128/1 C, 1 B, 1 R; 5/348 WB, 349

[56] References Cited

U.S. PATENT DOCUMENTS

| | | | |
|---|---|---|---|
| 1,943,888 | 1/1934 | Ewald | 128/24 R |
| 3,085,568 | 4/1963 | Whitesell | 5/370 |
| 3,317,934 | 5/1967 | Hinrichs | 5/349 |
| 3,335,717 | 8/1967 | Monaco | 128/33 |
| 3,392,723 | 7/1968 | Calvin | 5/108 |
| 3,419,923 | 1/1969 | Cowan | 128/33 UX |
| 3,428,973 | 2/1969 | Hargest et al. | 128/33 X |
| 3,602,186 | 8/1971 | Popenoe | 73/88 F |
| 3,672,354 | 6/1972 | Weber | 128/33 |
| 3,707,735 | 1/1973 | Carson | 5/370 |
| 3,736,604 | 6/1973 | Carson | 5/370 |
| 3,809,065 | 5/1974 | Gatts | 128/1 R |
| 3,872,526 | 3/1975 | Betts | 128/33 X |
| 3,993,042 | 11/1976 | Gatts | 128/1 B |

FOREIGN PATENT DOCUMENTS

| | | | |
|---|---|---|---|
| 164,040 | 9/1949 | Austria | 128/1 R |

*Primary Examiner*—Lawrence W. Trapp

*Attorney, Agent, or Firm*—Thomas E. Ciotti

[57] ABSTRACT

Method for imparting compensatory vestibular-proprioceptive stimulation to a premature infant to prevent apnea in which the infant is placed on a waterbed and random oscillations of low amplitude and predetermined frequency are generated in the bed by an oscillator placed under the bed.

3 Claims, 4 Drawing Figures

METHOD FOR TREATING PREMATURE INFANTS

This is a division, of application Ser. No. 639,288, filed Dec. 10, 1975 and now U.S. Pat. No. 4,048,684.

BACKGROUND OF THE INVENTION

1. Field of the Invention

This invention relates to a method for treating premature infants.

2. Description of the Prior Art

Vibrating waterbeds for adults are known. For instance, U.S. Pat. No. 3,872,526 describes a vibrating waterbed consisting of a rigid frame, a water-filled mattress contained within the frame, and a mechanical vibrator that is attached to the mattress.

Infant environment simulators and oscillating mattresses for infants are also known. The simulators are intended to artificially reproduce in utero conditions and normally include means for rocking the infant. For instance, U.S. Pat. No. 3,419,923 describes an air pad that is pressurized such that the baby is embraced by the pad rather than wholly supported by it. The pad is connected to a piston-driven air pump that pumps air into and out of the pad, thereby imparting motion to the pad. U.S. Pat. No. 3,672,354 similarly describes an infant air mattress that is pulsated at heartbeat frequency by a two-cycle pump. Such pulsations are said to have a quieting effect on the infant.

Rocking beds for infants are described in U.S. Pat. Nos. 2,776,658 and 2,869,538. These rocking beds generally consist of a crib containing a regular mattress and a rocking means that rocks the crib. Such rocking is said to assist the infant's respiration and circulation.

SUMMARY OF THE INVENTION

The invention is a method for treating a premature infant comprising providing a contained fluid medium on which the infant may be placed such that the infant is substantially wholly supported by the fluid medium, placing the infant on the contained fluid medium such that infant is so supported, and forming random oscillations in the fluid medium of low amplitude and predetermined frequency.

DETAILED DESCRIPTION OF EMBODIMENT OF DRAWINGS

Figure 1:
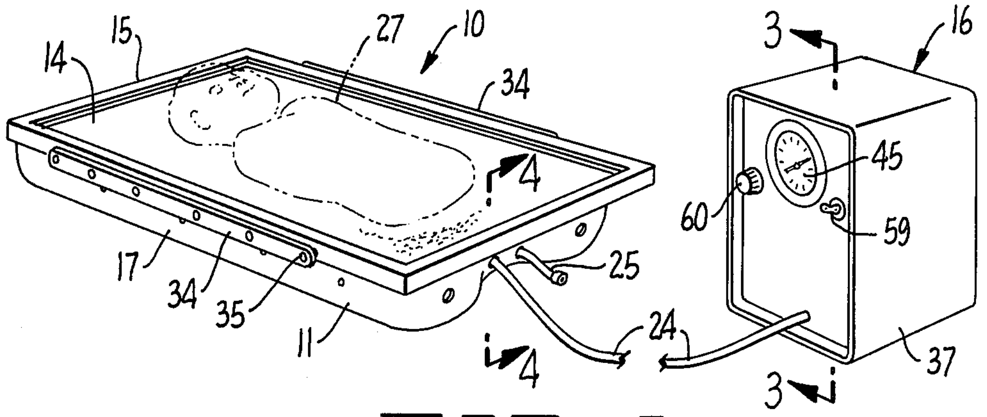
FIG. 1 is a dimetric view of an embodiment of the infant waterbed of the invention.
Figure 2:
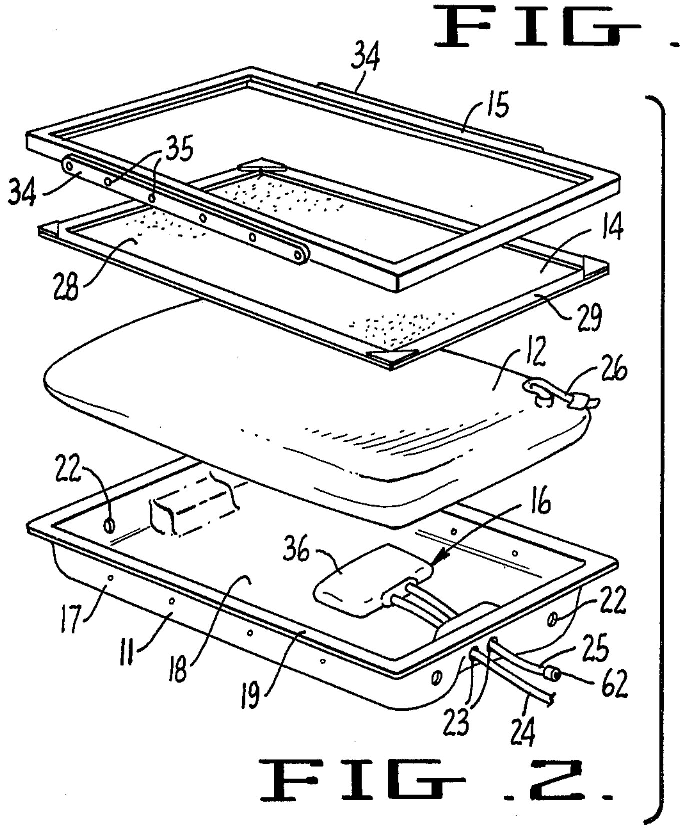
FIG. 2 is an exploded view of a portion of the waterbed of FIG. 1.

FIGS. 1 and 2 depict an infant waterbed, generally designated 10, that includes: a rigid tray 11, a flexible mattress 12 that contains a fluid medium 13 (FIG. 4), a tray cover 14, a frame 15, and an oscillator, generally designated 16. Waterbed 10 (minus oscillator 16) is sized to fit within a conventional incubator as a replacement for the standard incubator mattress.

Tray 11 serves as a container for mattress 12 and a site for the attachment of cover 14 and frame 15. It comprises a main body portion 17 that defines a recess 18, and a marginal ledge portion 19. Recess 18 is sized to contain mattress 12 and ledge portion 19 is sized to accommodate and receive the edge of cover 14, and frame 15. Tray 11 has a set of drain holes 22 in the event mattress 12 leaks or ruptures to emit fluid 13, and a pair of access holes 23 for receiving conduits 24, 25 of oscillator 16. Tray 11 may be made of any suitable rigid material such as plastic or stainless steel.

Mattress 12 is made from a flexible material that is impermeable to fluid 13. Preferably it is made from a sheet of flexible polymer such a polyvinyl chloride or a polyolefin. Mattress 12 is equipped with a port 26 through which fluid 13 may be charged and discharged. Fluid 13 may be gas, liquid or a medium such as beads that simulates a fluid and that will transmit the oscillations generated by oscillator 16. Preferably fluid 13 is a liquid and most preferably it is water. Fluid 13, when liquid, may be colored with a color not associated with body fluids, such as blue or green, to aid in the detection of mattress leaks, and should contain biocidal agents to inhibit organism growth. Mattress 12 is substantially filled with fluid 13, but no substantial pressure is built up within it. Thus, the walls of mattress 12 are not taut and an infant 27 (FIG. 1) will be substantially wholly supported by the fluid 13 contained within mattress 12.

Figure 4:
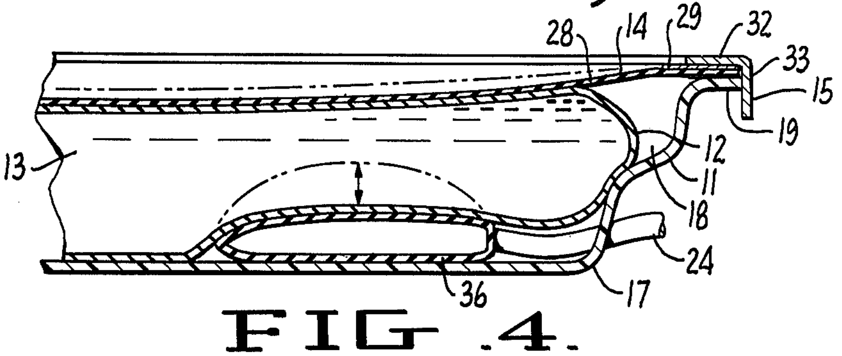
FIG. 4 is an enlarged cut-away sectional view taken through line 4—4 of FIG. 1.

Tray cover 14 serves to separate infant 27 from mattress 12. It is solely a safety factor in the event mattress 12 leaks or ruptures. In this regard it will prevent infant 27 from coming into contact with any fluid 13 that is emitted from mattress 12. Cover 14 includes a thin flexible sheet or membrane 28 surrounded by a peripheral border 29. Sheet 28 extends across and encloses recess 18 and border 29 sits on top of marginal ledge 19 of tray 11. Sheet 28 may be made of medical grade polymer sheeting, such as latex rubber sheet. Frame 15 holds cover 14 in place over the top of tray 11. As seen in FIG. 4 frame 15 comprises a horizontal element 32 and a vertical element 33. Border 29 is held firmly between ledge 19 and element 32 and vertical element 33 extends snugly down around the outer edge of ledge 19 to removably lock frame 15 into place over ledge 19.

Each longitudinal side of frame 15 has an elongated lateral bar 34 that is attached to it in spaced relationship by spacers 35. Bars 34 serve as sites for attaching infant immobilizing means (not shown) such as gauze strips that may be wrapped around the infant's extremities and tied or otherwise affixed to bars 34.

Oscillator 16 includes an expandable-compressible bladder 36 that sits in the bottom of tray 11 under mattress 12, and an oscillator control box or housing 37 (FIGS. 1 and 3) that is located remotely from tray 11. Conduit 24 connects bladder 36 to control box 37. Within box 37 is a second expandable-compressible bladder 38 that has two conduits 39, and 42 extending from it and that sits on the horizontal portion 43 of an L-shaped platform 44 mounted on the bottom of box 37. Conduit 24 connects through the front panel of box 37 with conduit 39. Conduit 42 is connected to a pressure gauge 45 whose face is visible on the front panel of box 37. A bladder depressor plate 46 is hinged to the front side of vertical portion 47 of platform 44 by a hinge 48. Plate 46 rests against the top of bladder 38. A single speed 60 rpm electrical motor 49 is mounted to the front side of vertical portion 47 above plate 46. The driving shaft of motor 49 has a disc 52 attached to it. One end of a link 53 is eccentrically and rotatably attached to disc 52 by a pin 54. The other end of link 53 is rotatably attached to a mounting 55 on the top of plate 46 by another pin 56.

Box 37 also contains a power circuit, indicated generally at 57, and a switch circuit, indicated generally at 58. Power circuit 57 is connected to line voltage and to motor 49 via switch circuit 58. Power circuit 57 is also connected to an on-off power switch 59 located on the front panel of box 37 (FIG. 1). Switch circuit 58 is connected to an oscillation frequency control switch 60 also located on the front panel of box 37. Power circuit 57 and switch circuit 58 turn motor 49 on for a one second interval and off randomly at an average, preselected (by switch 60) frequency. Both circuits may be made from conventional electrical and electronic components using circuit and logic schemes that are within the ordinary skill of the electronics art.

Figure 3:
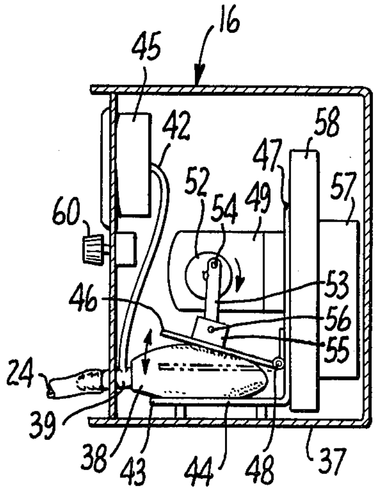
FIG. 3 is an enlarged sectional view taken through line 3—3 of FIG. 1.

Oscillator 16 operates as follows. Air is first pressured into bladders 36, 38 through a valve 62 on the end of conduit 25 to the desired pressure (shown on gauge 45). The pressure is such that bladder 36 in its normal state is at least partly deflated (shown in solid line in FIG. 4) due to the weight of mattress 12 and infant 27. An average oscillation frequency is then selected with switch 60 and the on-off power switch is turned to on, thus activating circuits 57, 58. As indicated above these circuits turn motor 49 on for a one second interval and then off randomly. Referring to FIG. 3, when motor 49 is turned on for one second, disc 52 makes one complete revolution. This first causes link 53 to be driven downwardly and depressor plate 46 to be correspondingly pivoted downwardly (shown in phantom in FIG. 3) and then causes link 53 to be driven upwardly and plate 46 to correspondingly be pivoted upwardly back to its original position (shown in solid line in FIG. 3). The downward movement of plate 46 compresses bladder 38 thereby forcing air therefrom through conduits 39, 24 into bladder 36 and causing bladder 36 to expand (shown in phantom in FIG. 4). The upward movement of plate 46 removes the compressive force from bladder 38 thereby allowing air to be forced from bladder 36 back through conduits 24, 39 into bladder 38 by the weight of mattress 12 and infant 27. Such expansion and deflation of bladder 36 distorts mattress 12 and generates oscillations (or waves) in the fluid 13 within mattress 12. The amplitude of the oscillations will depend on the relative volumes of bladder 36 (deflated and inflated) and mattress 12 and the shape of bladder 36. The amplitude is desirably quite low, that is usually less than about two cm. The frequency, of course, depends upon how often the motor 49 is turned on-off per unit time. Normally the frequency will be about 6 to 20 on cycles per minute, preferably 6 to 12 cycles per minute.

Infant waterbeds of this invention have been used to impart compensatory vestibular-proprioceptive stimulation to premature infants. In such treatment the infants (before the sixth postnatal day) were placed on the beds with their feet at the end of the mattress under which the oscillator bladder was placed. In this manner, the oscillations occur in a foot-to-head direction. The beds were positioned within a conventional incubator. The infants were kept on the bed for seven days and their clinical progress was compared to that of a control group of similar babies. The waterbed treatment had no significant effects on the infants' vital signs, weight, or frequency of emesis. However, highly significant differences were found in the incidence of apnea between the two groups, with the infants on the waterbeds having significantly fewer apneic spells than the infants of the control group. The randomness of the oscillations is considered to be important to such treatment since such oscillations provide a non-redundant stimulus that the infant is less likely to adapt to and "tune out". In this regard the terms "random" and its variants as used herein are not limited to denoting oscillation sequences that are random in a mathematical-statistical sense, but that include sequences that are sufficiently irregular to not become redundant to the infants. Thus these terms denote oscillation sequences that are truly random as well as irregular sequences that are repeated periodically.

The water temperature in the mattress is maintained by the incubator's heating system and the waterbeds have a more uniform temperature on their total surface than conventional incubator mattresses. This may provide better control of the temperature of the infant which will have beneficial effects on the infant's welfare.

Modifications of the above described method for treating premature infants that are obvious to those of ordinary skill in the mechanical, electrical, medical apparatus, and medical arts are intended to be within the scope of the following claims.

We claim:

1. A method for treating a premature infant comprising:

(a) providing a contained fluid medium on which the infant may be placed such that the infant is substantially wholly supported by the fluid medium;

(b) placing the infant on the contained fluid medium such that the infant is substantially wholly supported by the fluid medium; and (c) forming random oscillations in the fluid medium of low amplitude and predetermined frequency.

2. The method of claim 1 wherein the frequency is in the range of about 6 and 20 cycles per minute.

3. The method of claim 1 wherein the oscillations move from foot-to-head of the infant.

* * * * *